US011027882B2

(12) United States Patent
Bottger et al.

(10) Patent No.: US 11,027,882 B2
(45) Date of Patent: Jun. 8, 2021

(54) PRE-STERILIZABLE CARRIER SYSTEM

(71) Applicant: ARZNEIMITTEL GMBH APOTHEKER VETTER & CO. RAVENSBURG, Ravensburg (DE)

(72) Inventors: Frank Bottger, Ravensburg (DE); Benjamin Bobst, Mittelbiberach (DE)

(73) Assignee: ARZNEIMITTEL GMBH APOTHEKER VETTER & CO. RAVENSBURG, Ravensburg (DE)

( * ) Notice: Subject to any disclaimer, the term of this patent is extended or adjusted under 35 U.S.C. 154(b) by 0 days.

(21) Appl. No.: 16/383,847

(22) Filed: Apr. 15, 2019

(65) Prior Publication Data

US 2020/0262609 A1 Aug. 20, 2020

Related U.S. Application Data

(60) Continuation of application No. 14/136,305, filed on Dec. 20, 2013, now abandoned, which is a division of (Continued)

(30) Foreign Application Priority Data

Jun. 19, 2008 (DE) ..................... 10 2008 030 267.8

(51) Int. Cl.

*B65B 3/04* (2006.01)
*A61M 5/00* (2006.01)

(Continued)

(52) U.S. Cl.

CPC ............ *B65D 21/02* (2013.01); *A61J 1/2093* (2013.01); *B65B 3/003* (2013.01); *B65B 7/2821* (2013.01);

(Continued)

(58) Field of Classification Search

CPC .................. A61J 1/2093; A61M 5/284; A61M 2005/005; A61M 5/008; A61M 5/00; B65B 3/003; B65B 3/04

(Continued)

(56) References Cited

U.S. PATENT DOCUMENTS 3,696,579 A 10/1972 Narusawa et al.
3,807,119 A * 4/1974 Shields ............. A61M 5/31596 53/471

(Continued)

FOREIGN PATENT DOCUMENTS

DE 1962228 A1 11/1970
DE 10028823 A1 12/2001

(Continued)

OTHER PUBLICATIONS

English translation of First Office Action for corresponding Japanese Patent Application No. 2011-513939, dated Jan. 28, 2013 (3 pages).

(Continued)

*Primary Examiner* — Gloria R Weeks
(74) *Attorney, Agent, or Firm* — Stephen T. Olson; Harness, Dickey & Pierce, P.L.C.

(57) ABSTRACT

A method for filling dual-chamber systems in pre-sterilizable carrier systems includes providing at least one washed, siliconized and sterilized dual-chamber system in a magazine. The dual-chamber system includes respective separating elements separating the two chambers from each other. The magazine accommodates at least one dual-chamber system and is arranged in a container that is sealed with a closing element. The method additionally includes introducing the container into a clean room; opening the container and filling a first chamber of the at least one dual-chamber system; and closing the first chamber. The method further (Continued)

includes filling a second chamber of the at least one dual-chamber system; closing the second chamber; and removing the system from the clean room.

19 Claims, 6 Drawing Sheets

Related U.S. Application Data application No. 12/997,218, filed as application No. PCT/EP2009/004308 on Jun. 16, 2009, now Pat. No. 8,677,723.

(51) Int. Cl.

| | |
|---|---|
| ***B65D 21/02*** | (2006.01) |
| ***B65B 7/28*** | (2006.01) |
| ***B65B 3/00*** | (2006.01) |
| ***B65B 55/02*** | (2006.01) |
| ***A61J 1/20*** | (2006.01) |
| *A61J 1/06* | (2006.01) |

(52) U.S. Cl.
CPC ............ *B65B 55/027* (2013.01); *A61J 1/062* (2013.01); *A61J 1/2041* (2015.05)

(58) Field of Classification Search
USPC ............................................ 604/89; 220/500
See application file for complete search history.

(56) References Cited

U.S. PATENT DOCUMENTS

| | | | | |
|---|---|---|---|---|
| 4,058,213 | A | 11/1977 | Stone | |
| 4,059,109 | A * | 11/1977 | Tischlinger | A61M 5/284 604/88 |
| 4,135,561 | A | 1/1979 | Senelonge | |
| 4,716,710 | A | 1/1988 | Galy et al. | |
| 4,729,208 | A | 3/1988 | Galy et al. | |
| 5,080,649 | A | 1/1992 | Vetter | |
| 5,122,117 | A * | 6/1992 | Haber | A61M 5/284 604/201 |
| 5,435,076 | A | 7/1995 | Hjertman et al. | |
| 5,439,703 | A | 8/1995 | Kanda et al. | |
| 5,472,422 | A * | 12/1995 | Ljungquist | A61M 5/2448 604/89 |
| 5,788,670 | A | 8/1998 | Reinhard et al. | |
| 5,865,798 | A * | 2/1999 | Grimard | A61M 5/31596 604/89 |
| 6,189,292 | B1 | 2/2001 | Odell et al. | |
| 6,224,568 | B1 | 5/2001 | Morimoto et al. | |
| 6,263,641 | B1 | 7/2001 | Odell et al. | |
| 6,319,225 | B1 * | 11/2001 | Sugita | A61M 5/2448 604/89 |
| 6,363,641 | B1 | 4/2002 | Martinez | |
| 6,807,797 | B2 | 10/2004 | Forsberg et al. | |
| 6,991,002 | B2 | 1/2006 | Osborne et al. | |
| 7,232,038 | B2 | 6/2007 | Whitney | |
| 7,910,067 | B2 | 3/2011 | Knight et al. | |
| 8,002,734 | B2 * | 8/2011 | Bassarab | A61M 5/284 604/82 |
| 8,469,923 | B2 * | 6/2013 | Vedrine | A61M 5/3134 604/87 |
| 8,485,357 | B2 | 7/2013 | Song et al. | |
| 8,544,682 | B2 * | 10/2013 | Fransson | A61M 5/31501 222/1 |
| 8,763,350 | B2 * | 7/2014 | Bottger | B65B 3/003 53/440 |
| 9,862,519 | B2 | 1/2018 | Deutschle et al. | |
| 9,937,288 | B2 * | 4/2018 | Wright | A61M 5/14546 |
| 2005/0177100 | A1 | 8/2005 | Harper et al. | |
| 2006/0151629 | A1 * | 7/2006 | Vedrine | B05B 11/02 239/329 |
| 2007/0060875 | A1 | 3/2007 | Bassarab et al. | |
| 2009/0018496 | A1 | 1/2009 | Harper et al. | |
| 2010/0262074 | A1 | 10/2010 | Seiferlein et al. | |
| 2011/0094189 | A1 | 4/2011 | Bottger et al. | |
| 2012/0323173 | A1 | 12/2012 | Thorne, Jr. et al. | |
| 2013/0105346 | A1 | 5/2013 | Ramkhelawan et al. | |
| 2014/0224834 | A1 * | 8/2014 | Bartlett, II | A61J 1/2093 222/82 |
| 2017/0267383 | A1 * | 9/2017 | Werk | B65B 3/003 |

FOREIGN PATENT DOCUMENTS

| | | | |
|---|---|---|---|
| DE | 10341978 | A1 | 9/2004 |
| DE | 102005038458 | A1 | 2/2007 |
| EP | 0440846 | A1 | 8/1991 |
| EP | 0882441 | A2 | 12/1998 |
| JP | H08224305 | | 9/1996 |
| JP | 2002505921 | A | 2/2002 |
| JP | 2005521478 | A | 7/2005 |
| JP | 2009-504293 | A | 2/2009 |
| WO | WO-99/045985 | A1 | 9/1999 |
| WO | WO-2003082369 | A2 | 10/2003 |
| WO | WO-2005/039669 | A2 | 5/2005 |
| WO | WO-2006028562 | A2 | 3/2006 |
| WO | WO-2009/153018 | A1 | 12/2009 |

OTHER PUBLICATIONS

International Search Report and Written Opinion of the ISA/ISA/, Rijswijk, NL, dated Sep. 15, 2009.
Brazilian Search Report dated Sep. 4, 2018 for file PCT/EP/2009/004308.
Inernational Search Report for PCT/EP2009/004313, Rijswijk, NL, dated Oct. 1, 2009.
English translation of International Preliminary Report on Patentability for PCT/EP2009/004313, incorporating the English translation of the Written Opinion of the ISA.
English translation of International Preliminary Report on Patentability for PCT/EP2009/004308, incorporating the English translation of the Written Opinion of the ISA.
Office Action regarding China Patent Application No. 2011-513939 dated Jan. 31, 2014.

* cited by examiner

PRE-STERILIZABLE CARRIER SYSTEM

CROSS-REFERENCE TO RELATED APPLICATIONS

This application is a continuation of U.S. Divisional patent application Ser. No. 14/136,305 filed 20 Dec. 2013, which is a divisional of U.S. patent application Ser. No. 12/997,218 filed 9 Dec. 2010, which is a 371 U.S. National Stage of International Application No. PCT/EP2009/004308 filed 16 Jun. 2009, which claims priority to German Patent Application No. 10 2008 030 267.8 filed 19 Jun. 2008. The disclosures of the above applications are expressly incorporated herein by reference.

DESCRIPTION

The invention relates to a method for filling dual-chamber systems in pre-sterilizable carrier systems and to a pre-sterilizable carrier system.

Pre-sterilizable carrier systems and methods for filling the same are known. A known carrier system comprises usually washed siliconized and sterilized syringes which are placed in a magazine after the washing and siliconizing step. The magazine—also called nest—is subsequently inserted into a container which is then sealed with a closing element, preferably a gas-permeable membrane film, and sterilized via suitable sterilization methods. Here, an ethylene oxide gassing is frequently used. Because the closing element is gas-permeable, the sterilization gas can penetrate into the interior of the container and can also sterilize the content of the container, thus the washed and siliconized syringes as well as the magazine comprising the latter. After the sterilization step, the container does not need to be opened again and can be delivered in the present form directly to a customer or can be transferred to a filling line. The gas-permeable closing element has in fact a filter effect in such a manner that it is permeable for a sterilization gas, but closes the container in a tight and sterile manner with respect to germs, viruses and bacteria. As long as the container remains closed, the sterility of its content is therefore ensured. At the customer who typically operates a filling system for filling the syringes or other hollow bodies having a pharmaceutical content comprised by the container, the container is opened, the hollow bodies are filled and closed, whereupon also the container can be closed again and can be transported to the end customer. Of course, the filled and closed hollow bodies can also be removed from the container and can be delivered to the end customer in different packaging units. It is essential in the mentioned pre-sterilized carrier systems and the methods for filling the same that a standardized packaging form is used which can be used in connection with standardized filling lines. Thus, the hollow bodies to be filled do not need to be removed from the container prior to the filling, whereby a complicated work step is eliminated. Furthermore, it is advantageous that the hollow bodies can be sterilized together in already packaged form, whereupon an immediate delivery or further processing can take place without the need of complicated intermediate steps such as packing into a new pre-sterilized further packaging unit or repacking. On the part of a producing pharmaceutical company which performs the filling, a clean room or the work step for preparing the hollow bodies can be eliminated because the latter are delivered ready for filling.

The fabrication and/or preparation of the hollow bodies can also take place as in-line process with the filling if a hot-air tunnel is provided between the sterilization device and the clean room in which the filling takes place.

However, the known pre-sterilizable carrier systems and the methods for filling the same are designed only for single-chamber systems, thus single-chamber syringes, single chamber carpules or phials. In order to fill dual-chamber systems such as dual-chamber syringes or carpules, complex methods and carrier devices are still necessary.

It is therefore the object of the invention to provide a method for filling at least one dual-chamber system in a pre-sterilizable carrier system.

The object underlying the invention is solved by a method with the features of the claim 1.

Said method is characterized by the following steps: Provided is at least one washed, siliconized and sterilized dual-chamber system which is arranged in a magazine, the dual-chamber system comprising respective separating elements separating the two chambers from each other, the magazine accommodating the at least one dual-chamber system, preferably a number of such systems, wherein the magazine is arranged in a container sealed with a closing element. The sealed container is introduced into a clean room. There, the container is opened and a first chamber of the at least one dual-chamber system is filled. The first chamber is closed and a second chamber of the at least one dual-chamber system is filled. The second chamber is also closed and the at least one filled dual-chamber system is removed from the clean room. By using standardized pre-sterilizable carrier systems, a producing pharmaceutical company is relieved of the complex preparation of the hollow bodies, and the use of standardized filling lines is possible.

The object underlying the invention is also solved by a method with the features of the claim 2.

Said method is characterized by the following steps: Provided is at least one washed, siliconized and sterilized dual-chamber system which has a separating element separating the two chambers from each other. A magazine accommodates the at least one dual-chamber system, preferably a number of such systems, wherein the magazine is arranged in a container which is sealed with a closing element. The container is introduced into a clean room. The container is opened and the first chamber of the at least one dual-chamber system is filled. The container is closed with a gas-permeable closing element. A method step follows in which the material contained in the first chamber of the at least one dual-chamber system is lyophilized. Here, the solvent vapor sublimates through the gas-permeable closing element of the container. After the lyophilization, the container is opened and the first chamber of the at least one dual-chamber system is closed. A second chamber of the at least one dual-chamber system is filled and closed. The at least one filled dual-chamber system is removed from the clean room.

Also preferred is a method which is characterized in that the magazine which accommodates the at least one dual-chamber system comprises plastic and preferably consists of plastic. Hereby, the magazine is very light and thus easy to handle. It can also be configured as product for a one-time use so that it can be disposed of after its use. Thus, the heavy metal magazine which are typical for the known carrier systems and which, on the one hand, are difficult to handle and, on the other, are difficult to autoclave to maintain them sterile, are eliminated. In contrast, in case of the carrier systems according to the invention, with each new delivery, a new plastic magazine is supplied which is allocated to precisely one dual-chamber system or a batch of dual-chamber systems and is disposed of after its use. Apart from the elimination of complex work steps, this results in that with respect to its sterility, an easily reproducible handling of dual-chamber systems is possible.

Also preferred is a method in which the container comprises plastic and preferably consists of plastic. Here too is preferably addressed that the container is used once and is disposed of after its use. To each batch of dual-chamber systems, one container is unambiguously allocated so that here too, the sterility of the batches is ensured with very high reproducibility.

Also preferred is a method which is characterized in that the closing element for the container is gas-permeable. This addresses, on the one hand, the closing element with which the container is delivered to the filling station. This closing element is preferably gas-permeable so that the container can be pre-sterilized in the already closed state at the manufacturer. The closing element is indeed configured to be permeable for sterilization gases but not for germs, viruses or bacteria. On the other hand, the closing element is addressed with which the container is closed before a possible lyophilization step is carried out. This closing element is preferably gas-permeable so that the solvent vapor released during the lyophilization can sublimate through the closing element and thus can leave the space enclosed by the container. It is preferred that both closing elements are configured as gas-permeable membrane films.

Preferred is also a method in which the container, after filling the first chamber of the at least one dual chamber system and closing it with a gas-permeable closing element, is first removed from the clean room and then introduced into a device for lyophilizing arranged outside of the clean room. There, the lyophilization takes place, after the completion of which the container is removed from the device and is introduced again into a clean room. If this step is added to the method, it is possible to completely separate the aseptic filling of the pharmaceutical content from the lyophilization, wherein the same does no longer need to be carried out in an aseptic manner. This is possible because the container is provided with a gas-permeable closing element which allows the sublimated solvent vapor during the lyophilization process to pass from the interior of the container to the outside, but prevents germs, viruses and bacteria from penetrating into the container. The interior of the container thus remains aseptic even if the environment in the lyophilizer is not sterile. In this manner, complex cleaning and disinfection steps for the lyophilizer can be eliminated and the latter does not need to be arranged within the clean room.

Also, in this connection, a method is preferred which is characterized in that the lyophilization device itself is not sterile and/or aseptic. As mentioned, this is possible by closing the container with a gas-permeable closing element which, however, is not permeable for viruses, bacteria and germs.

Further advantageous configurations with respect to the claimed method arise from the sub-claims.

It is also the object of the invention to provide a pre-sterilizable carrier system for at least one dual-chamber system.

This object is solved by a pre-sterilizable carrier system with the features of the claim 12. The carrier system comprises at least one washed, siliconized and sterilized dual-chamber system which has a separating element separating the two chambers from each other. Furthermore, the pre-sterilizable carrier system comprises a magazine which serves for accommodating a dual-chamber system. It also comprises a container. The magazine which accommodates the at least one dual-chamber system can be arranged in the container, wherein the latter can be sealed with a closing element. In this manner, a closed container is created in which a magazine is arranged which comprises at least one washed, siliconized and sterilized dual-chamber system. It is particularly preferred if the entire container is sterilized in its interior. Due to the sealing, such pre-sterilized carrier systems equipped with dual-chamber systems can be produced ahead and stored, wherein the content remains sterile.

Also preferred is a pre-sterilizable carrier system, wherein the magazine comprises plastic and preferably consists of plastic. In this case, the magazine is particularly light and, moreover, is disposable after the use of the pre-sterilizable carrier system so that complex cleaning and autoclaving steps are eliminated. Also, each batch of dual-chamber systems is allocated to precisely one magazine so that a highly reproducible handling with respect to the sterility is possible.

Also preferred is a pre-sterilizable carrier system which is characterized in that the container comprises plastic and preferably consists of plastic. Also in this case, the container is provided for a one-time use so that each batch of dual-chamber systems is allocated to precisely one container. This too increases the reproducibility of the handling with respect to its sterility.

Furthermore, a pre-sterilizable carrier system is preferred in which the closing element for the container is gas-permeable. In this case, the container already equipped with the magazine and the at least one dual-chamber system can be closed at the manufacturer and can subsequently be sterilized in that the gas intended for the sterilization penetrates through the gas-permeable closing element into the interior of the container. After the sterilization it is not necessary anymore to open the container and the same can be transported immediately, for example, to a filling line. Due to the fact that the container is already finally closed, a subsequent opening or closing does not result in that germ-containing material penetrates from outside into the interior of the container. Here, the term gas-permeable addresses that the closing element allows gases and vapors to pass through, but prevents germs, viruses or bacteria from penetrating into the interior of the container.

The invention is illustrated in more detail hereinafter by means of the drawings. In the figures.

Figure 1:
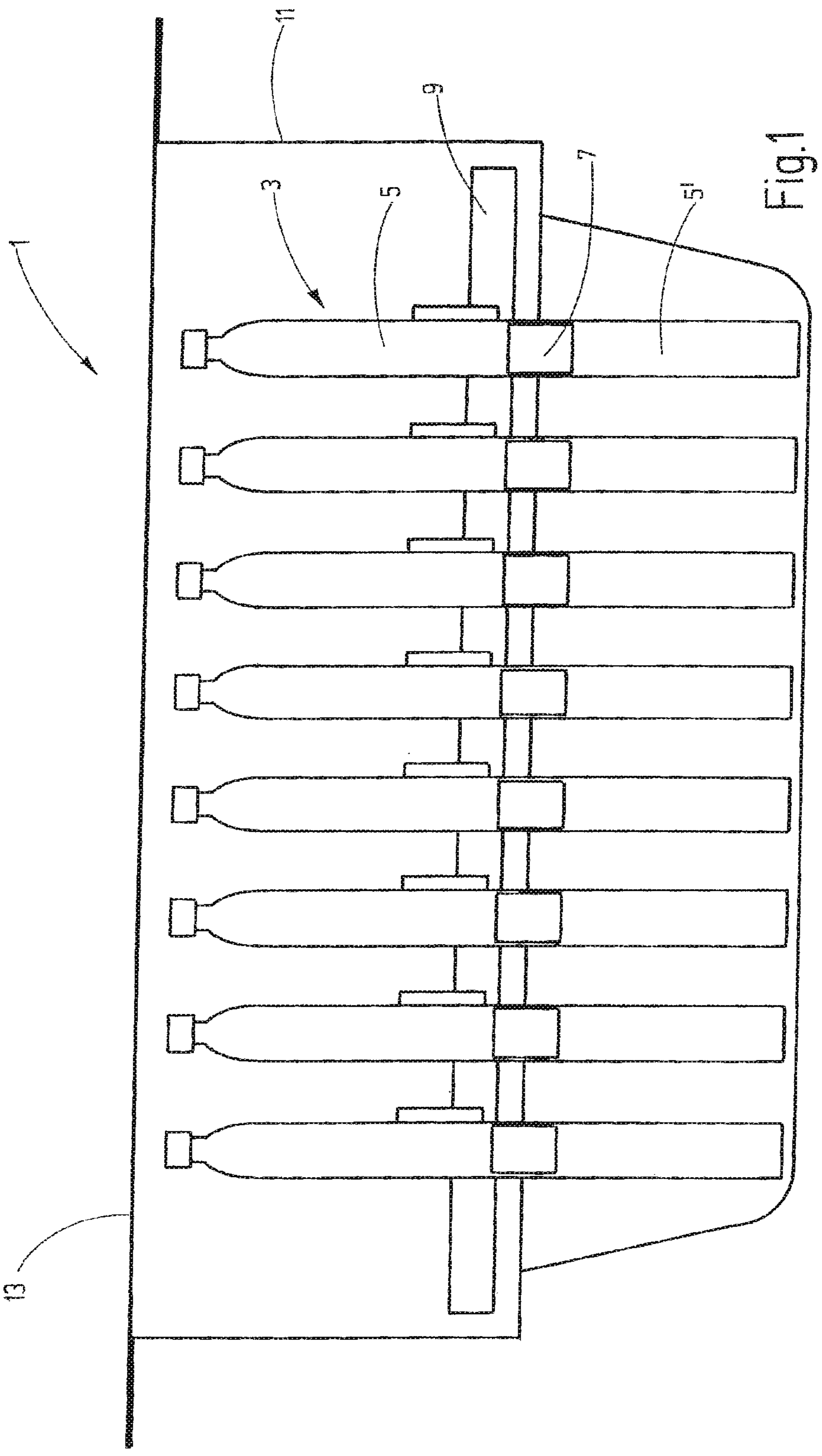
FIG. 1 shows a schematic view of a pre-sterilizable carrier system.

FIG. 1 shows schematically an exemplary embodiment of a pre-sterilized carrier system. The pre-sterilizable carrier system 1 comprises at least one washed, siliconized and sterilized dual-chamber system 3 with two chambers 5, 5' which are separated from each other by a separating element 7. The dual-chamber systems 3 are accommodated by a magazine 9 which in turn can be arranged in a container 11. The latter is sealed with a closing element 13.

The container 11 can comprise plastic and preferably consists of plastic. The magazine 9 too can comprise plastic and preferably consists of plastic. In this manner, both elements can be provided for a one-time use so that to each batch of dual-chamber systems 3, one magazine 9 and one container 11 are allocated.

The closing element 13 for the container 11 is preferably configured in a gas-permeable manner so that the fully loaded and sealed container 11 can be sterilized in the closed state by introducing the container into an atmosphere which comprises a gas intended for sterilization or a vapor intended for sterilization. The gas or the vapor can penetrate through the closing element 13 into the interior of the container 11 and thus can sterilize in particular the interior of the container 11 and the dual-chamber systems 3 and the magazine 9 contained therein.

The different methods are now illustrated in more detail by means of the FIGS. 2 to 5.

First, the pre-sterilizable carrier system 1 is provided and introduced into a clean room. Then, the closing element 13 is removed so that the dual-chamber systems 3 are accessible.

Figure 2:
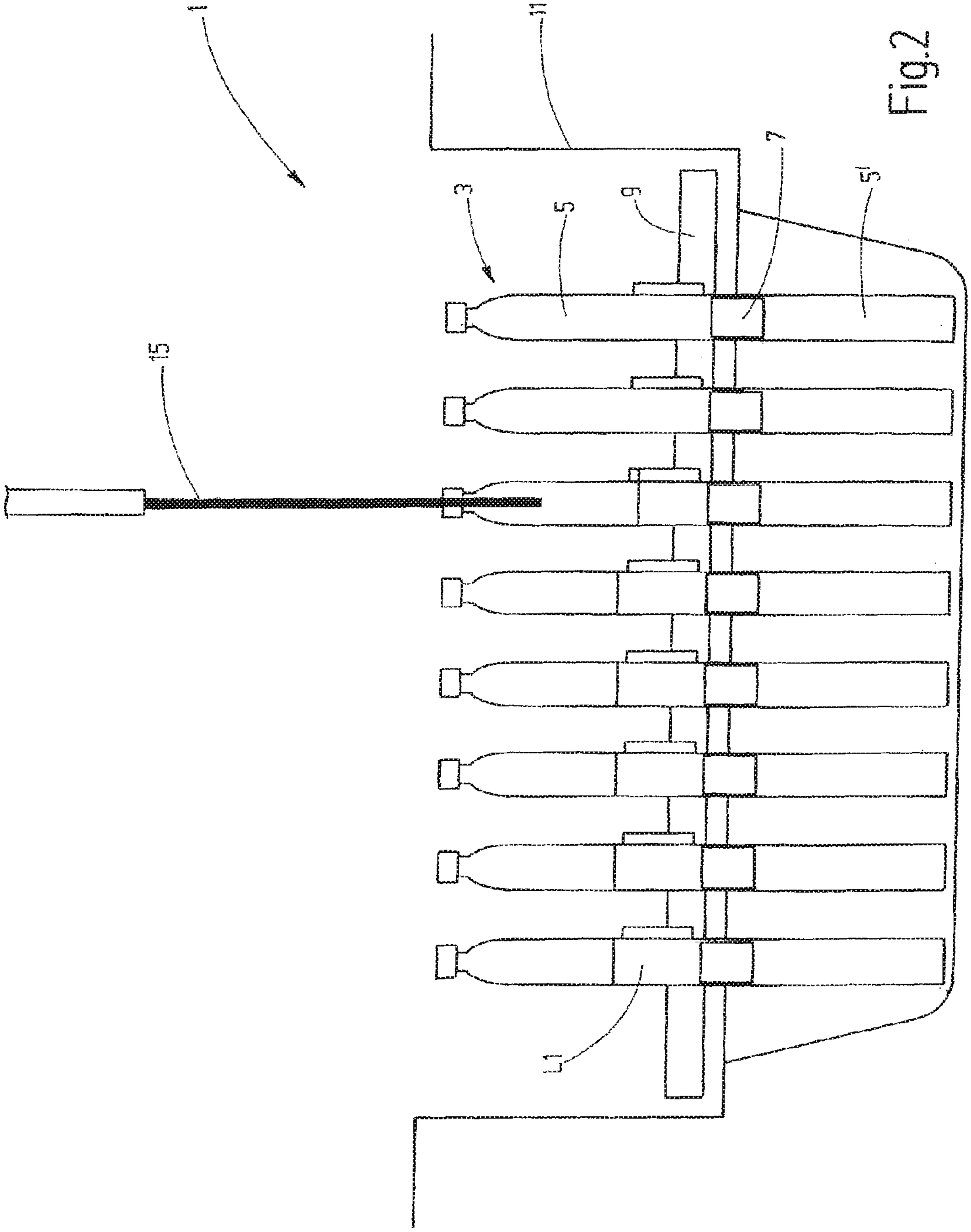
FIG. 2 shows a schematic illustration of the step of filling a first chamber of the dual-chamber systems with a method according to the invention.

FIG. 2 shows the step of filling a first chamber 5 of the dual-chamber systems 3. Identical and functionally identical elements are indicated with identical reference numbers so that in this respect, reference is made to the preceding description. A dispensing device 15 is provided through which a first solution L1 of an active and/or auxiliary substance can be introduced into a first chamber 5 of the dual-chamber systems 3.

Figure 3:
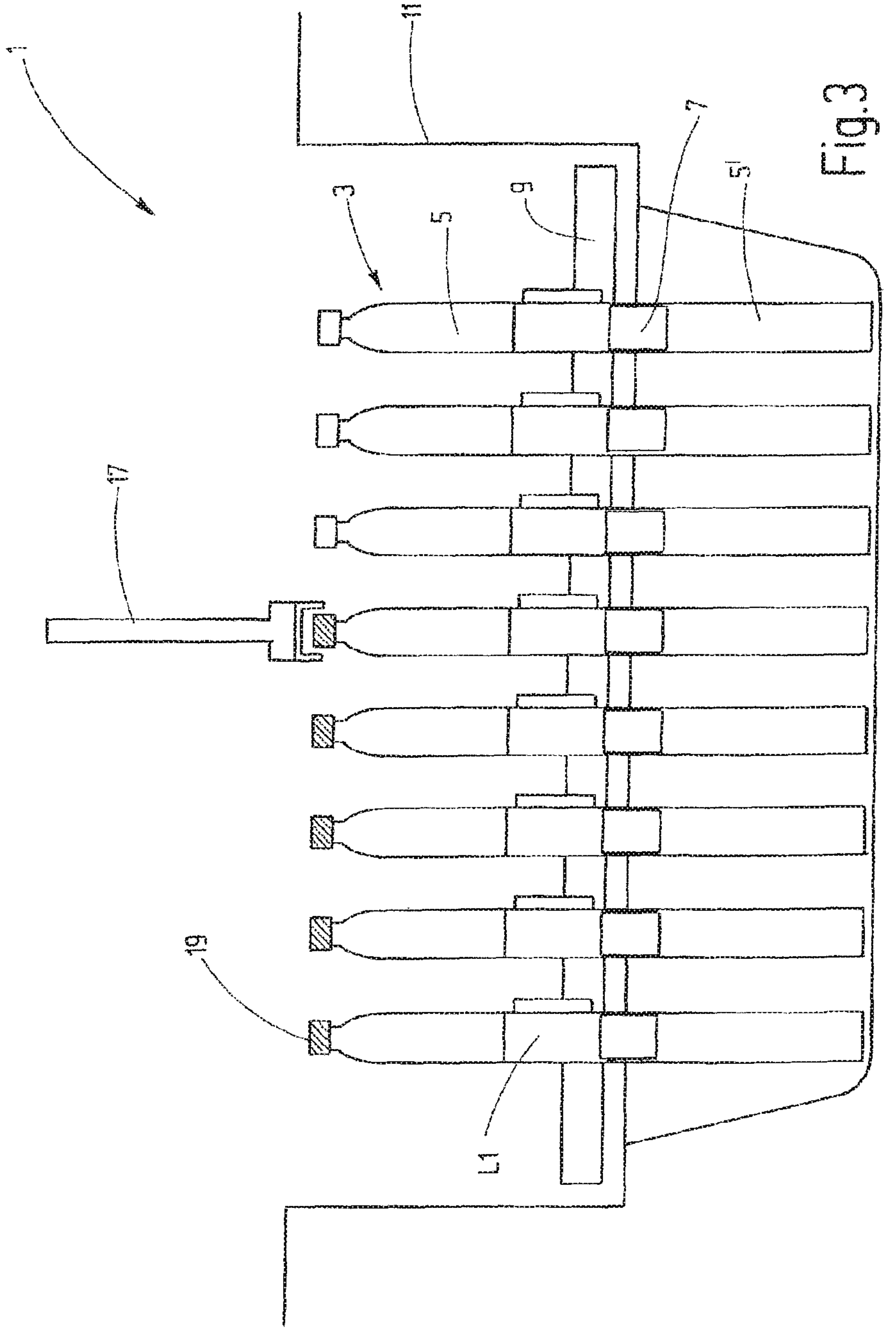
FIG. 3 shows a schematic view of the closing process of the first chamber of the dual-chamber systems with the method.

After filling the first chamber 5 of the dual-chamber systems 3, the first chamber can be closed as shown in FIG. 3. Identical and functionally identical elements are indicated with identical reference numbers so that in this respect, reference is made to the preceding description. A first closing device 17 is provided by means of which the first chamber 5 of the dual-chamber systems 3 can be closed in each case with one closure 19. The closure 19 can be a flanged cap, a tamper-proof closure, a closure with attachable needle or a closure with attached needle. In principle, other types of closures can also be used; it is essential, however, that the first chamber 5 of the dual-chamber system 3 is tightly sealed by a closure 19.

Instead of closing the first chamber 5 of the dual-chamber systems 3 directly after filling it is also possible to integrate a lyophilization step for the active substance and/or auxiliary substance contained in the solution L1. For this purpose, the container 11 is closed after filling the first chamber 5 of the dual-chamber systems 3 with a gas-permeable closing element, preferably a gas-permeable membrane film. The container 11 sealed in this manner can be introduced into a lyophilization device where the solution contained in the first chamber 5 sublimates through the gas-permeable closing element so that the active substance and/or auxiliary substance present in the dual-chamber systems 3 is lyophilized. Since the container 11 is hygienically sealed by the gas-permeable closing element 13, it is possible to provide the lyophilization device outside of the clean room. Thus, the container 11 can be removed from the clean room and can be introduced into an external lyophilization device. The latter does not have to be sterile and/or aseptic because no germs, viruses or bacteria can pass through the closing element 13 and get into the interior of the container 11. In this manner, in particular the dual-chamber systems 3 remain sterile or aseptic even if the lyophilization is carried out in a non-sterile and/or non-aseptic environment. After lyophilization, the container 11 can be introduced again into a clean room in which the further method steps take place.

Of course, it is also possible to arrange the lyophilization device in the clean room itself so that removing and re-introducing the container 11 is eliminated. It is obvious that here also the lyophilization device itself has to be sterile and/or aseptic.

During lyophilization, the dual-chamber systems 3 are embedded in the container 11 and are reliably protected against interfering radiation or other disturbing influences.

If such a lyophilization step is integrated between the filling of the first chamber 5 of the dual-chamber systems 3 and the closing of said first chamber, it is obvious that the container 11—if necessary, after re-introducing into a clean room—has to be opened again so that the dual-chamber systems 3 are accessible. After closing the first chamber 5 of the dual-chamber systems, a second chamber 5' is filled. This is possible in a particularly simple manner by turning the magazine 9 over. In this case it is provided that the magazine 9 encompasses the dual-chamber systems 3 in such a manner that the latter are securely retained in the magazine 9, independent of the orientation of the same. In this manner it is ensured that the dual-chamber systems 3 do not slip out of the magazine, not even when turning it over. After turning the magazine 9 over, the same is preferably introduced again into the container 11, wherein now a second chamber 5' of the dual-chamber systems 3 is accessible through the opening of the container 11.

Figure 4:
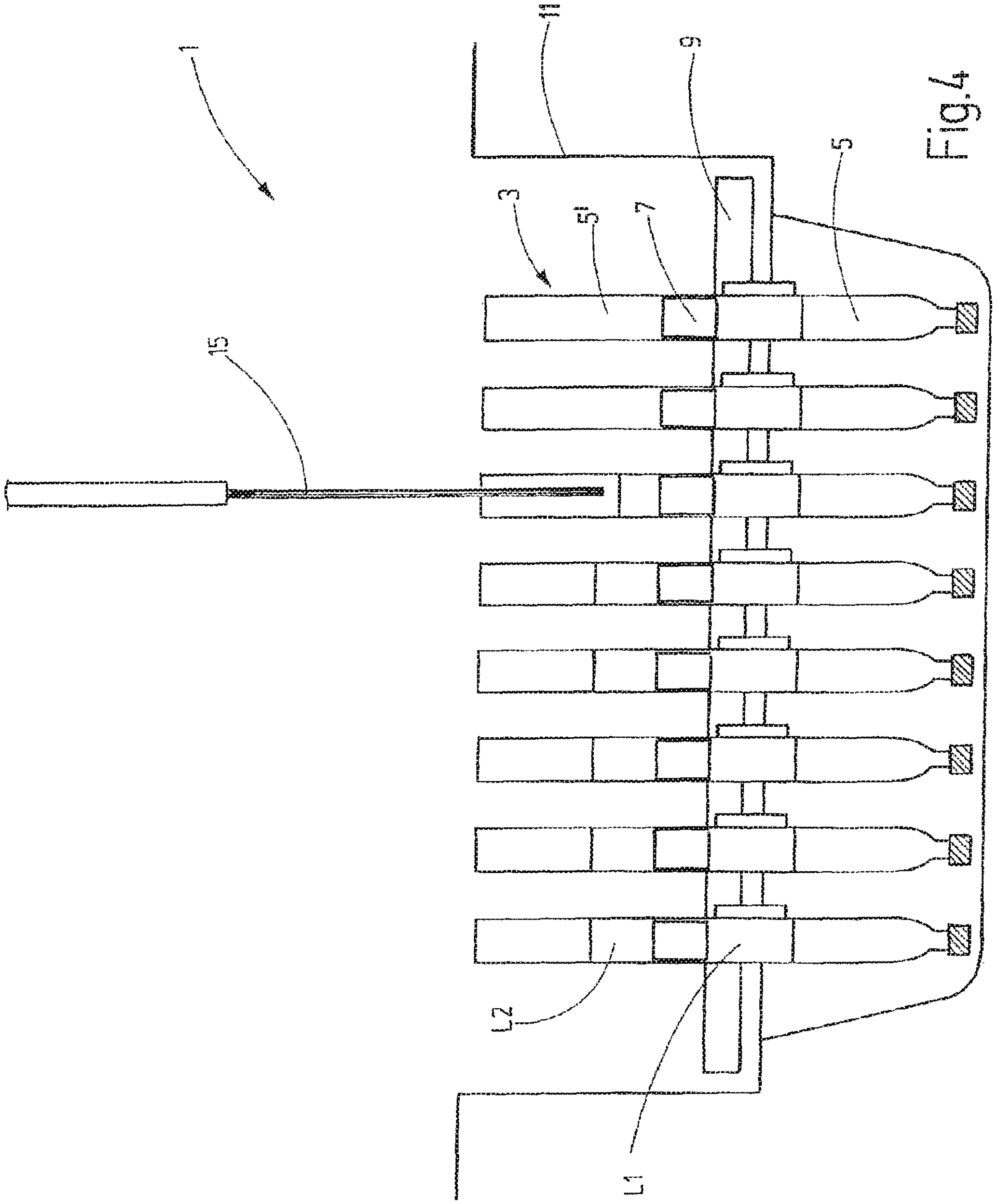
FIG. 4 shows a schematic illustration of the filling process of a second chamber of the dual-chamber systems with the method.

FIG. 4 shows schematically the filling of the second chamber 5 of the at least one dual-chamber system 3. Identical and functionally identical elements are indicated with identical reference numbers so that in this respect, reference is made to the preceding description. Here too, a dispensing device 15 is provided through which a second medium L2 can be introduced into the second chamber 5' of the dual-chamber systems 3. The second medium L2 can involve the solution of a further active substance and/or auxiliary substance; however, it can also involve a—preferably pure—solvent or solvent mixture.

After filling the second chamber 5' of the dual-chamber systems 3, said chamber can also be closed.

Figure 5:
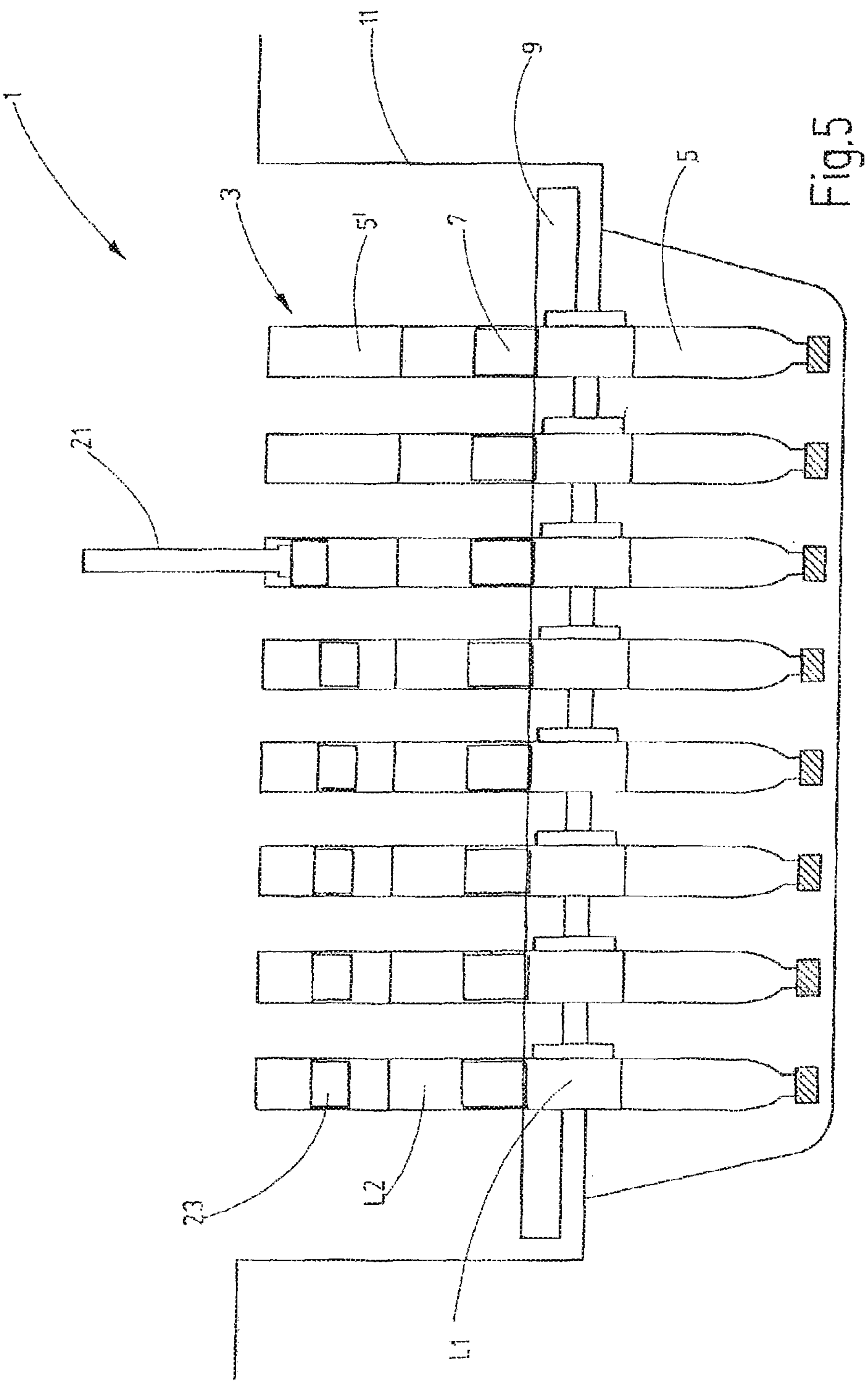
FIG. 5 shows the closing process of the second chamber of the dual-chamber system with the method.
Figure 6A:
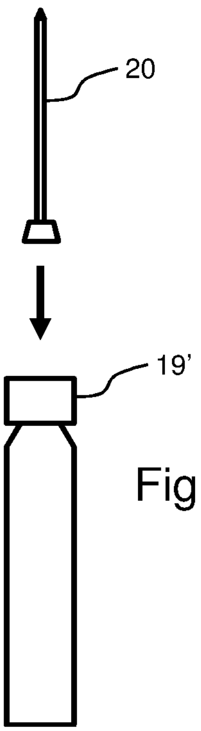
FIG. 6A illustrates an alternative closure with attachable needle.
Figure 6B:
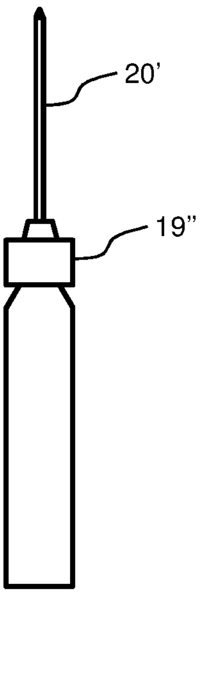
FIG. 6B illustrates another alternative closure with attached needle.

FIG. 5 shows schematically the step of closing the second chamber 5' of the dual-chamber systems 3. Identical and functionally identical elements are indicated with identical reference numbers so that in this respect, reference is made to the preceding description. The second chamber 5' is closed by means of a second closing device 21 with a closing element which is exemplary configured here as plug 23. The latter is preferably displaceable in the dual-chamber system 3 so that pressure forces can be transmitted via the plug into the second chamber 5' and finally into the separating element 7, wherein the pressure forces result in an activation of the dual-chamber system 3. It is preferred that the plug 23 is configured as threaded plug. In this manner, it can act as plunger element, wherein a non-illustrated plunger rod can be engaged by means of an external thread with the internal thread of the threaded plug 23. Thus, pressure forces can be transmitted in a very simple manner into the second chamber 5' and therefore indirectly into the separating element 7, wherein the pressure forces result in an activation of the dual-chamber systems 3.

After closing the second chamber 5', the container 11 can be closed again and can be removed from the clean room. It is also possible to omit the closing of the container 11 and to selectively remove the container in its open state from the clean room or to remove only the magazine 9 or even the individual dual-chamber systems 3 from the clean room. Since both chambers 5, 5' of the dual-chamber systems 3 are tightly sealed, it is not required to keep the dual-chamber systems 3 any longer in a sterile and/or aseptic environment.

Overall, it is apparent that the production method according to the invention and the pre-sterilizable carrier system according to the invention are advantageous over the known methods and devices for filling dual-chamber systems. According to the invention it is possible for a producing pharmaceutical company to use a standardized packing directly on standardized filling lines. Here, it is also possible to fill products intended for lyophilization on plants which are configured for pre-sterilizable systems. In known methods, specifically for filling dual-chamber systems in connection with materials intended for lyophilization, heavy and expensive metallic magazines are used which are re-used and therefore have to be autoclaved in a costly manner. In the present case, instead of such magazines, a standardized packing form is used during the entire filling process, wherein the packing form is used only once and is disposed of afterwards. Since the carrier system according to the invention is gas-permeable but can be sealed to be impenetrable for germs, viruses or bacteria, it is possible to arrange the filling area and the lyophilization area decentralized with respect to each other which, moreover, allows to carry out the lyophilization in a non-sterile environment. The content of the carrier system according to the invention thus remains sterile at any time. Furthermore, in known methods it is necessary to close each individual chamber 5, 5' of the dual-chamber systems 3 prior to the lyophilization step with a so-called lyo closure, whereby the selection of the closure of the first chamber is limited. In contrast, in the present method it is possible to select any closure system. This is achieved by the fact that the container 11 itself is closed by a gas-permeable closing element 13 so that an individual closing of the first chamber 5 of the dual-chamber systems 3 is not necessary for the lyophilization step. Since during the semi-automatic, automatic or manual loading and unloading of the lyophilizer, hygienically closed containers are handled, there is again a significantly lower contamination risk as this is the case with known methods.

The invention claimed is:

1. A method of filling at least one dual-chamber system having a first chamber with a first sealable opening and a second chamber with a second sealable opening, each dual-chamber system further including a separating element separating the first chamber from the second chamber, the method comprising:

securely retaining the at least one dual-chamber system in a container with a magazine in a first orientation, such that each dual-chamber system of the at least one dual-chamber system is securely retained in a first configuration relative to the container with the first opening facing upwardly and the second opening facing downwardly;

introducing a first solution into the first chamber of the at least one dual-chamber system through the first opening;

inverting each dual-chamber system of the at least one dual-chamber system such that each dual-chamber system is securely retained in a second configuration relative to the container with the second opening facing upwardly and the first opening facing downwardly; and introducing a second solution into the second chamber of the at least one dual-chamber system through the second opening;

wherein inverting each dual-chamber system of the at least one dual-chamber system includes:

removing the magazine from the container with each dual-chamber system securely in the magazine independent of an orientation of the magazine;

turning the magazine over to a second orientation; and returning the magazine to the container with each dual-chamber system in the second configuration.

2. The method of filling at least one dual-chamber system of claim 1, wherein the first solution is selected from an active substance, an auxiliary substance and combinations thereof.

3. The method of filling at least one dual-chamber system of claim 2, wherein the second solution is selected from an active substance, an auxiliary substance and combinations thereof.

4. The method of filling at least one dual-chamber system of claim 2, wherein the second solution is selected from a solvent, and a solvent mixture.

5. The method of filling at least one dual-chamber system of claim 2, further comprising sealing the container with a gas-permeable closing element.

6. The method of filling at least one dual-chamber system of claim 5, wherein the gas permeable closing element reversibly seals an upper side of the container with the magazine arranged in both of the first and second orientations.

7. The method of filling at least one dual-chamber system of claim 6, further comprising:

introducing the container into a clean room with the at least one dual-chamber system sealed within the container by the gas-permeable closing element; and removing the gas-permeable closing element to provide filling access to the at least one dual-chamber system.

8. The method of filling at least one dual-chamber system of claim 7, further comprising: resealing the container with the gas-permeable closing element after introducing the first solution into the first chamber of the at least one dual-chamber system and before removing the magazine from the container; and lyophilizing the first solution.

9. The method of filling at least one dual-chamber system of claim 8, wherein lyophilizing the first solution occurs within the clean room.

10. The method of filling at least one dual-chamber system of claim 9, further comprising removing the container from the clean room, wherein lyophilizing the first solution occurs outside the clean room.

11. The method of filling at least one dual-chamber system of claim 10, further comprising returning the container to the clean room prior to introducing the second solution into the second chamber of the at least one dual-chamber system.

12. The method of filling at least one dual-chamber system of claim 1, further comprising closing the second chamber of the at least one dual-chamber system after introducing the second solution into the second chamber.

13. The method of filling at least one dual-chamber system of claim 12, wherein closing the second chamber includes closing the second chamber with a plug.

14. The method of filling at least one dual-chamber system of claim 13, wherein each each dual-chamber system of the at least one dual-chamber system such that each dual-chamber system includes a separating element separating the first and second chambers.

15. The method of filling at least one dual-chamber system of claim 14, wherein closing the second chamber includes displacing the plug within the dual-chamber system so that pressure forces are transmitted via the plug into the second chamber and finally into the separating element such that the pressure forces activate the dual-chamber system.

16. The method of filling at least one dual-chamber system of claim 1, wherein the at least one dual-chamber system includes a plurality of dual-chamber systems.

17. The method of filling at least one dual-chamber system of claim 1, wherein the container has an upper side, a lower side, and a shoulder in a middle region between the upper side and the lower side, the lower side being closed by a bottom wall of the container, the upper side being open.

18. The method of filling at least one dual-chamber system of claim 1, wherein the container includes a shoulder having an abutment surface abutting the magazine in both the first orientation and the second orientation.

19. The method of filling at least one dual-chamber system of claim 1, wherein the magazine includes a first planar side and an opposing second planar side, and further wherein the first planar side faces upward in the first configuration and the second planar side faces upward in the second configuration.

* * * * *